US 8,758,768 B2
Jun. 24, 2014

(12) United States Patent
Kristiansen et al.

(54) PROCESS FOR PRODUCTION OF FUNGAL EXTRACELLULAR IMMUNE STIMULATING COMPOUNDS

(75) Inventors: Bjoern Kristiansen, Frederikstad (NO); David Waddell, Glasgow (GB)

(73) Assignee: Glycanova AS, Gamle Fredrikstad (NO)

( * ) Notice: Subject to any disclaimer, the term of this patent is extended or adjusted under 35 U.S.C. 154(b) by 0 days.

(21) Appl. No.: 12/896,726

(22) Filed: Oct. 1, 2010

(65) Prior Publication Data

US 2011/0045026 A1    Feb. 24, 2011

Related U.S. Application Data

(63) Continuation of application No. 10/488,427, filed as application No. PCT/IB02/03557 on Sep. 3, 2002, now abandoned.

(30) Foreign Application Priority Data

Sep. 3, 2001 (NO) .................................... 20014256

(51) Int. Cl.
A61K 36/07 (2006.01)

(52) U.S. Cl.
USPC ...................... 424/195.15; 424/274.1; 514/54

(58) Field of Classification Search
None
See application file for complete search history.

(56) References Cited

U.S. PATENT DOCUMENTS

| | | | |
|---|---|---|---|
| 3,943,247 A | 3/1976 | Komatsu | |
| 3,987,166 A | 10/1976 | Komatsu | |
| 4,207,312 A | 6/1980 | Fujii et al. | |
| 4,247,541 A | 1/1981 | Ishida et al. | |
| 4,454,289 A | 6/1984 | Nakajima et al. | 536/123.12 |
| 4,461,760 A | 7/1984 | Sugano | |
| 4,769,363 A | 9/1988 | Misaki et al. | |
| 4,962,094 A | 10/1990 | Jamas et al. | |
| 5,032,401 A | 7/1991 | Jamas et al. | |
| 5,223,491 A | 6/1993 | Donzis | |
| 5,283,239 A | 2/1994 | Koga et al. | |
| 5,322,841 A | 6/1994 | Jamas et al. | |
| 5,397,773 A | 3/1995 | Donzis | |
| 5,488,040 A | 1/1996 | Jamas et al. | |
| 5,504,079 A | 4/1996 | Jamas et al. | |
| 5,519,009 A | 5/1996 | Donzis | |
| 5,532,223 A | 7/1996 | Jamas et al. | |
| 5,576,015 A | 11/1996 | Donzis | |
| 5,607,677 A | 3/1997 | Jamas et al. | |
| 5,622,939 A | 4/1997 | Jamas et al. | |
| 5,622,940 A | 4/1997 | Ostroff et al. | |
| 5,633,369 A | 5/1997 | Jamas et al. | |
| 5,641,761 A | 6/1997 | Takahashi | |
| 5,663,324 A | 9/1997 | James et al. | |
| 5,702,719 A | 12/1997 | Donzis | |
| 5,705,184 A | 1/1998 | Donzis | |
| 5,741,495 A | 4/1998 | Jamas et al. | |
| 5,744,187 A | 4/1998 | Gaynor | |
| 5,756,318 A | 5/1998 | Kosuna | |
| 5,811,542 A | 9/1998 | Jamas et al. | |
| 5,817,643 A | 10/1998 | Jamas et al. | |
| 5,849,720 A | 12/1998 | Jamas et al. | |
| 6,020,324 A | 2/2000 | Jamas et al. | |
| 6,046,323 A | 4/2000 | Park | |
| 6,084,082 A | 7/2000 | Ravikumar et al. | |
| 6,084,092 A | 7/2000 | Wakshull | |
| 6,090,615 A | 7/2000 | Nagaoka | |
| 6,090,938 A | 7/2000 | Wakshull et al. | |
| 6,110,692 A | 8/2000 | Wakshull et al. | |
| 6,110,892 A | 8/2000 | Barbier et al. | |
| 6,117,850 A | 9/2000 | Patchen et al. | |
| 6,143,731 A | 11/2000 | Jamas et al. | |
| 6,294,321 B1 | 9/2001 | Wakshull et al. | |
| 6,369,216 B1 | 4/2002 | Patchen et al. | |
| 6,413,715 B2 | 7/2002 | Wakshull et al. | |
| 6,440,448 B1 | 8/2002 | Intelisano | |
| 6,630,310 B1 | 10/2003 | Wakshull et al. | |
| 7,022,685 B2 | 4/2006 | Patchen et al. | |
| 2001/0051717 A1 | 12/2001 | Wakshull et al. | |
| 2002/0164317 A1 | 11/2002 | Gorsek | |
| 2002/0164773 A1 | 11/2002 | Wasser et al. | |
| 2003/0208796 A1 | 11/2003 | Song et al. | |
| 2005/0002962 A1 | 1/2005 | Pasco et al. | |

(Continued)

FOREIGN PATENT DOCUMENTS

| | | |
|---|---|---|
| CN | 1082551 | 2/1994 |
| CN | 1297994 | 6/2001 |

(Continued)

OTHER PUBLICATIONS

Aoki et al.: "Antibodies to HTVLV I and III in sera from two Japanese patients, one with possible pre-aids" The Lancet, Oct. 20, 1984.
Aoki, "Lentinan", Immune Modulation Agents and Their Mechanisms, Editors: Fenichel and Chirigos, Marcel Dekker, Inc. 1984, pp. 63-77.
Chihara et al.: "Antitumour Polysaccharide derived Chemically from Natural Glucan (Pachyman)" Nature, vol. 225, Mar. 7, 1970.
Chihara, "The antitumor polysaccharide Lentinan: an overview", Manipulation of Host Defence Mechanisms, Editors: Aoki et al., Excerpta Medica 1981, pp. 1-16.
Hamuro J. et al., "Carboxymethylpachymaran, a New Water Soluble Polysaccharide with Marked Antitumour Activity", Nature vol. 233, Oct. 15, 1971.

(Continued)

*Primary Examiner* — Satyendra Singh
(74) *Attorney, Agent, or Firm* — McLane, Graf, Raulerson & Middleton, PA

(57) ABSTRACT

A process is described for the production of an immunostimulant by submerged cultivation of *Lentinus edodes* in which mycelium from agar plates or a fermentation broth is added to a liquid medium in a shake flask or a bioreactor containing nutrients such as malt extract, yeast extract, peptone and glucose having access to air or to which air is added, and which is kept in constant movement at approx. 28° C. At the proper conditions, there will be an increase in the production of extracellular lentinan, which is shown to be a better immunostimulant than intracellular lentinan. The extracellular product is precipitated from the growth medium by means of methods for the precipitation of microbial polysaccharide.

12 Claims, No Drawings

(56) References Cited

U.S. PATENT DOCUMENTS

| | | | |
|---|---|---|---|
| 2005/0130273 | A1 | 6/2005 | Versali et al. |
| 2005/0158258 | A1 | 7/2005 | Fisher |
| 2005/0238654 | A1 | 10/2005 | Takeda |
| 2005/0245480 | A1 | 11/2005 | Ostruff et al. |
| 2006/0159698 | A1 | 7/2006 | Murata et al. |
| 2007/0041994 | A1 | 2/2007 | McDowell, Jr. |
| 2007/0104728 | A1 | 5/2007 | Rangel et al. |
| 2007/0172934 | A1 | 7/2007 | Muller et al. |
| 2007/0178118 | A1 | 8/2007 | Goino |
| 2008/0063650 | A1 | 3/2008 | Yan |
| 2008/0103112 | A1 | 5/2008 | Magee et al. |
| 2008/0106114 | A1 | 5/2008 | Wheatley |
| 2008/0167268 | A1 | 7/2008 | Yan |

FOREIGN PATENT DOCUMENTS

| | | |
|---|---|---|
| CN | 1314417 | 9/2001 |
| CN | 1477130 | 2/2004 |
| CN | 1490016 | 4/2004 |
| CN | 1528335 | 9/2004 |
| CN | 1765935 | 3/2006 |
| EP | 0 292 601 | 11/1988 |
| EP | 0 298 706 | 1/1989 |
| EP | 0 370 673 | 5/1990 |
| EP | 0 382 551 | 8/1990 |
| EP | 1155623 | 11/2001 |
| JP | 5653101 | 5/1981 |
| JP | 06172217 | 6/1994 |
| JP | 7173070 | 7/1995 |
| JP | 63296662 | 12/1998 |
| JP | 2001-07814 | 3/2001 |
| JP | 2002060344 | 2/2002 |
| JP | 2004300438 | 3/2004 |
| KR | 2003097062 | 2/2005 |
| SU | 1244179 A | 7/1986 |
| WO | WO 89/12106 | 12/1989 |
| WO | WO 8912106 | 12/1989 |
| WO | WO 91/06307 | 5/1991 |
| WO | WO 96/15659 | 5/1996 |
| WO | WO 00/32212 | 6/2000 |
| WO | WO 00/32213 | 6/2000 |
| WO | WO 00/54795 | 9/2000 |
| WO | WO 00/65029 | 11/2000 |
| WO | WO 0151070 | 7/2001 |
| WO | WO 01/64057 | 9/2001 |
| WO | WO 01/82935 | 11/2001 |
| WO | WO 02/07708 | 1/2002 |
| WO | WO 02/087603 | 11/2002 |
| WO | WO 02/098440 | 12/2002 |
| WO | WO 03/020944 | 3/2003 |
| WO | WO 03/043440 | 5/2003 |
| WO | WO 03/080077 | 10/2003 |
| WO | WO 2004/075907 | 9/2004 |
| WO | WO 2004/100965 | 11/2004 |
| WO | WO 2006/007848 | 1/2006 |

OTHER PUBLICATIONS

Jong, S.C., and Birmingham, J.M. "Medicinal and Therapeutic Value of the Shiitake Mushroom". Advances in applied microbiology, 1993, vol. 39, pp. 153-184, XP008056557.

Sasaki et al.: "Further study of the structure of lentinan, an anti-tumor polysaccharide from *Lentinus edodes*" Carbohydrate Research, 47 (1976) 99-104.

Suzuki et al., "Structural Characterization of the Immunoactive and Antiviral Water-solubilized Lignin in an Extract of the Culture Medium of *Lentinus edodes* Mycelia (LEM)", Agric. Biol. Chem., 54 (2), 479-487, 1990.

Suzuki et al.: "Induction of endogenous lymphokine-activated killer activity by combined administration of lentinan and interleukin 2" Int. J. Immunopharmac., vol. 12, No. 6, pp. 613-623, 1990.

Tokimoto, K.: "Lysis of the mycelium of *Lentinus edodes* caused by mycolytic enzymes of *Trichoderma harzianum* when the two fungi were in an antagonistic state", Trans. Mycol. Soc. Japan 23: 13-20, 1982.

Suzuki, et al., "Antiviral and Interferon-Inducing Activities of a New Peptimomannan, KS-2, Extracted From Culture Mycelia of *Lentinus edodes*", The Journal of Antibiotics, vol. XXXII, No. 12, pp. 1336-1345, Dec. 1979.

Maeda, et al., "Denaturation and Renaturation of a $\beta$-1,6;1,3-Glucan, Lentinan, Associated with Expression of T-Cell-mediated Responses", Cancer Research, vol. 48, pp. 671-675, Feb. 1, 1988.

Fujii, et al., "Isolation and characterization of a new antitumor polysaccharide, KS-2, extracted from culture mycelia of *Lentinus edodes*", The Journal of Antibiotics, vol. 31(11), pp. 1079-1090, Nov. 1978.

Maeda, et al., "Unique increase of serum proteins and action of antitumour polysacchardies", Nature, vol. 252, pp. 250-252, Nov. 15, 1974.

Chihara, et al., "Fractionation and Purification of the Polysaccharides with Marked Antitumor Activity, Especially Lentinan, from *Lentinus edodes* (Berk.) Sing. (an Edible Mushroom)", Cancer Research, vol. 30, pp. 2776-2781, Nov. 1970.

Yamashita, et al., "Intestinal absorption and urinary excretion of antitumor peptidomannan KS-2 after oral administration in rats", Immunophamacology, vol. 5, pp. 209-220, 1983.

Brauer et al. Effects of Management on the Yield and High-Molecular-Weight Polysaccharide Content of Shiitake (*Lentinus edodes*) Mushrooms. J Agric Food Chem 2002, pp. 5333-5337, vol. 50.

Elisashvili et al. Extracellular Polysaccharide Production by Culinary-Medicinal Shiitake Mushroom *Lentinus edodes* (Berk.) Singer and *Pleurotus* (Fr.) P. Karst. Species Depending on Carbon and Nitrogen Source. International Journal of Medicinal Mushrooms, 2004, pp. 165-172, vol. 6.

Zorn et al. Enzymatic hydrolysis of carotenoid esters of marigold lowers (*Tagetes erecta* L.) and red paprika (*Capsicum annuum* L.) by commercial lipases and *Pleurotus sapidus* extracellular lipase. Enzyme and Microbial Technology, 2003, pp. 623-628, vol. 32, Elsevier.

Lee et al. Submerged culture conditions for the production of mycelial biomass and exopolysaccharaides by the edible Basidiomycete *Grifola frondosa*. Enzyme and Microbial Technology 2004, pp. 369-376, vol. 35, Elsevier.

Kondhkar et al. Sugar profile of extracellular polysaccharides from different *Tremella* species. International Journal of Food Microbiology.2002, pp. 121-129, vol. 79, Elsevier.

Hsieh et al. Production of polysaccharides of *Ganoderma lucidum* (CCRC36021) by reusing thin stillage. Process Biochemistry 2005 vol. 40.

Shu et al. Monitoring the polysaccharide quality of agaricus blazei in submerged culture by examining molecular weight distribution and TNF-alpha release. Biotechnology Letters 2003 pp. 2061-2064 vol. 25.

Fan et al. Effect of nutrional and envirnmentak conditions on the production of exopolysaccharide of araricus brasiliensis by submerged fermentation and its anti-tumor activity. LWT 2005 pp. 30-35, vol. 40.

Wang, Tze-Hua, et al., "*Lentinus* Products and Patents in China". Medimush internal document, compiled from information retrieved from internet Aug.-Sep. 2006.

Lee, et al. "Structural Analysis of the Antitumor Active Exo-polysaccharide Produced by Submerged Cultivation of *Ganoderma lucidum* Mycelium", The Korean Journal of Mycology, vol. 27, No. 1, pp. 76-81, Feb. 1999. English abstract.

Li, et al., "Isolation, Purification and Bioactivities of Exopoly Saccharides from Fermented Broth of *Ganoderma lucidum*", Acta Microbiologica Sinica, vol. 40, No. 2, pp. 217-220, Apr. 2000. English abstract.

Yang, et al., "Hepatoprotective Effect of exo-polysaccharide Produced from Submerged Mycelial Culture of *Ganoderma lucidum* WK-003 by Using Industrial Grade Medium", The Korean Journal of Mycology, vol. 27, No. 1, pp. 82-86, Feb. 1999. English abstract.

Yang, et al., "The influence of environmental conditions on polysaccharide formation by *Ganoderma lucidum* in submerged cultures", Process Biochemistry, vol. 33, No. 5, pp. 547-553, 1998.

(56) References Cited

OTHER PUBLICATIONS

Kim, S.W., et al. "Mycelial growth and exo-biopolymer production by submerged culture of various edible mushrooms under different media". Letters in applied Microbiology, 2002, 34, 56-61, XP001051185.

Jong, S.C., and Birmingham, J.M. "Medicinal and Therapeutic Value of the Shiitake Mushroom". Advances in applied microbiology, 1993. vol. 39. 1993, pp. 153-184, XP008056557.

Zhang, L., et al. "Correlation between antitumor activity, molecular weight, and conformation of lentinan" Carbohydrate Research, 340, (2005), 1515-1521.

Lobanok et al. Composition and biological activity of submerged mycelium of the xylotrophic basidiomycete *Lentinus edodes*. Applied Biochemistry and microbiology, vol. 39, No. 1, 2003, p. 60-64 (translated from Priki Biokhi Mikkrobiol Jan.-Feb. 2003, 39(1):60-64).

Van Nevel et al. "The influence of *Lentinus edodes* (Shiitake muhroom) preparations on bacteriological and morphological aspects of the small intestine in piglets" Archives of animal nutrition—archive fur tierernahrung 57(6):399-412, Dec. 2003 (abstract).

Kawazoe T, et al. "Influence of an excessive supply of vitamin D-2 fortified shiitake mushroom on laying hens" Journal of the Japanese Society for food and science technology—Nippon Shokuhin Kagaku Kaishi 44(4) :300-305, 1997 (Abstract).

Gou FC, et al. "Effects of mushroom and herb polysaccharides, as alternatives for an antibiotic, on the cecal microbial ecosystem in broiler chickens" Poultry Science 83(2):175-182 Feb. 2004 (abstract).

Gou et al. "Immunoactive, medicinal properties of mushroom and herb polysaccharides and their potential use in chicken diets" Worlds poultry science journal 59(4) : 427-440 Dec. 2003 (abstract).

Nikl L et al. "Influence of 7 immunostimulants on the immne-response of Coho Salmon to Aeromonas-salmonicida", Diseases of Aquatic organisms 12(1): 7-12 Dec. 5, 1991 (Abstract).

MediMush Science Documents. C. Immune modifiers from the shiitake mushroom. Downloaded from Medimush website Jun. 2005, pp. 1-9, Oct. 2004.

Song CH, et al. Anti-complementary activity of endo-polymers produced from submerged mycelial culture of higher fungi with particular reference to *Lentinus edodes*. Biotechnology Letters, vol. 20, No. 8, Aug. 1998, pp. 741-744.

Chang R. Functional Properties of Edible Mushrooms. Nutrition Reviews, vol. 54, No. 11. Nov. 1996: S91-S93.

Borchers A., et al. Mushrooms, Tumors, and Immunity: An update., Experimental Biology and Medicine, 229:393-406 (2004).

MediMush Science Documents. L. HIV/AIDS. Downloaded from Medimush website Jun. 2005 (www.medimush.dk), pp. 1-3, Oct. 2004.

MediMush Science Documents. K. Tuberculosis. Downloaded from Medimush website Jun. 2005 (www.medimush.dk), pp. 1-2, Oct. 2004.

Mizuno T. The extraction and development of antitumor-active polysaccharides from medicinal mushrooms in Japan [Review]. International Journal of Medicinal Mushrooms 1999;1:9-30.

MediMush Science Documents. H. Lentinan taken orally. Downloaded from Medimush website Jun. 2005 (www.medimush.dk), pp. 1-5, Oct. 2004.

Harvey, L et al. Production of Lentinan by Submerged Cultivation of *Lentinus edodes* (Berk.) Sing. Int. Jour. of Medicinal Mushrooms, vol. 3, p. 161(2001).

S. Aouadi et. al., "Structural analysis and rheological behaviour of an extracellular polysaccharide from *Drechslera spicifera*", *Carbohydrate Polymers*, vol. 17 pp. 177-183, 1992.

Giovanni Giovannozzi Sermanni et. al., "The Production of Exo-Enzymes by *Lentinus edodes* and *Pleurotus ostreatus* and their use for Upgrading Corn Straw", *Bioresource Technology*, vol. 48, pp. 173-178, 1994.

Byung-Keun Yang et. al., "Hypoglycemic Effect of a *Lentinus edodes* Exo-polymer Produced from a Submerged Mycelial Culture", *Biosci. Biotechnol. Biochem.*, vol. 66:5, pp. 937-942, 2002.

Nora Hatvani, "Antibacterial effect of the culture fluid of *Lentinus edodes* mycelium grown in submerged liquid culture", *International Journal of Antimicrobial Agents*, vol. 17, pp. 71-74, 2001.

Zhou Weidong et. al., "Biological activity of hydrosoluble exopolysaccharide (HEP) from *Lentinus edodes* CL-2 by submerged fermentation", *Junwu Xitong*, vol. 16, No. 3, p. 202-207, 1997.

Zheng Xueyu et al., "Immune function of the extracellular and intracellular polysaccharides of *Lentinus edodes*", *Zhongcaoyao*, vol. 16, No. 11, p. 494-497, 1985.

Jong SC and Birmingham JM, "Medicinal and therapeutic value of the Shiitake Mushroom". Advnaces in Applied Microbiology, 1993, vol. 39: 153-184. entire document.

Tan YH and Moore D. "Convenient and effective methods for in vitro cultivation of mycelium and fruiting bodies of *Lentinus edodes*" Mycol. Res., 1992, 96(12): 1077-1084, abstract, materials & methods, and results & discussion.

Wasser SP and Weis AL, Medicinal properties of substances occuring in higher basidiomycetes mushrooms: current perspectives (Review). International Journal of Medicinal Mushrooms, 1999, vol. 1: 31-62, entire document.

Zheng X et al. "Immune function of the extracellular and intracellular polysaccharides of *Lentinus edodes* in normal mice". Zhongcaoyao, 1985, 16(11): 494-7, English translation for entire document provided.

The term "Extracellular"—Merriam-Webster Online Dictionary, at www.m-w.com. p. 1, Dec. 24, 2005.

J.E. Smith, N. J. Rowan, and R. Sullivan, "Chapter 5: Extraction, development and chemistry of anti-cancer components from medicinal mushrooms", in Medicinal Mushrooms: Their Therapeutic Properties and Current Medical Usage with Special Emphasis on Cancer Treatments, published by Cancer Research UK, 2001.

PROCESS FOR PRODUCTION OF FUNGAL EXTRACELLULAR IMMUNE STIMULATING COMPOUNDS

CROSS-REFERENCE TO RELATED APPLICATIONS

This application is a continuation application of U.S. patent application Ser. No. 10/488,427, filed on Mar. 3, 2004, now abandoned, which in turn is a national stage application of International Application No. PCT/IB2002/03557, filed on Sep. 3, 2002, which further claims priority from Norwegian Patent Application No. 20014256, filed on Sep. 3, 2001, each of which is incorporated herein by reference in its entirety.

TECHNICAL AREA OF THE INVENTION

The present invention is directed to a method for producing an immune stimulant in liquid culture. The invention is in one embodiment directed to culturing Lentinus edodes under particular conditions in a fermentation broth. This application is a non-provisional claiming priority from Norwegian patent application No. NO 2001 4256 filed 3 Sep. 2001, which is hereby incorporated by reference in its entirety. All patent and non-patent references cited in that application, or in the present application, are also hereby incorporated by reference in their entirety.

BACKGROUND OF THE INVENTION

It is known that health-promoting effects are attributed to glucans from fungi and yeasts. "Shiitake" fungus (Lentinus edodes) has been attributed effects which can be exploited for many medicinal purposes such as immunestimulation, anti-virus, anti-tumour, etc. Studies of lentinan have shown that it stimulates the immune system of the host in a variety of ways, such as activation of T helper cells, increased production of Interleukin 1 and Interleukin 2, increased antibody production in various forms of cancer, and decreasing the cholesterol level in the blood. (Herbs for Health, jan/feb, 1997; K. Jones, "Shiitake: Medicine in a mushroom", p. 40-50, 54; Anticancer Res, Vol. 17(4A), 1997; H. Matsouka, "Lentinan potentiates immunity and prolongs the survival time of some patients", p. 2751-2755; Adv Appl Microbiol, Vol. 39, 1993; S. C. Jong, "Medicinal and therapeutic value of the shiitake mushroom", p. 153-184, Int J Immunopharmacol, Vol. 14, 1992; K. Irinoda, "Stimulation of microbiocidal host defence mechanism against aerosol influenza virus infection by lentinan, p. 971-977., Jpn J Cancer Res, Vol. 76(1), 1985; D. Herlyn, "Monoclonal antibody-dependent murine macrophage-mediated cytotoxicity against human tumors is stimulated by lentinan, p. 37-42).

One active ingredient of Lentinus edodes is termed lentinan, a polysaccharide based compound described as a beta-(1,3) glucan backbone with beta-(1,6) side chains.

"Solid-state" reactors are routinely used for culturing fungi such as Lentinus edodes. This is a technology which is used for many purposes such as composting, production of biological products such as enzymes, soy sauce, acetic acid, and the like.

For the production of lentinan, Lentinus edodes can be cultivated on a suitable solid matrix provided by stems of tree or chips of wood to which is often added chemical compounds supporting the growth of mycelium and development of the fruiting bodies, where most of the lentinan is localised. The fruiting bodies are harvested, either by hand or mechanically, and are subsequently dried and ground to a powder which can be used as it is, or used in tablets, or sent for further processing such as extraction of lentinan.

The methods used for culturing fungi such as Lentinus edodes, harvesting and subsequently drying the fruiting bodies, and optionally extraction of lentinan, are well known for the skilled person. The cultivation time can be from four to ten weeks with few possibilities for controlling the process. This results in a fungal growth, and in turn, in an amount of lentinan produced which is not the same for each batch carried out. Also, extraction of lentinan from the fungal material is time consuming and process intensive.

Kim et al. (2001, Biotechnology Letters, 23, 513-517) describes extracellular polysaccharides produced by Phellinus lintus in submerged culture; Kim et al. (2002: Letters in Applied Microbiology, 34, 56-61) describes mycelial growth and exobiopolymer production by submerged culture of various edible mushrooms. There is no data available to indicate that any of these extracellular polymers are immune stimulating.

It is generally known to grow mycelium of Basidiomycetes in submerged culture and to obtain active ingredients from the growth medium, see e.g. Aouadi et al 1992 (Carbohydr Polym 17:177-184) and Lee et al 1995 (Prog Plant Polym Carbohydr Res, B. Behrs Verlag, Hamburg, Del.) and Hatvani 2001 (Int J Antimicrob Agents 17:71-). However, none of the references discloses the isolation of extracellular components with immune stimulating activities. Furthermore, none of the references disclose that extracellular polysaccharides have different activities from their intracellular counterparts.

It is therefore an object of the present invention to provide novel methods for production of extracellular immune stimulating agents with higher level of activity than the hitherto known intracellular counterparts.

SUMMARY OF THE INVENTION

The invention in a first aspect, relates to a method for cultivating a fungal mycelium, preferably a fungus from the class of basidiomycetes, such as a fungus of the genus Lentinus, such as Lentinus edodes, in a liquid medium of sterile water to which nutrient compounds are added in predetermined concentrations. The liquid medium supports fungal growth and stimulates the production of extracellular compounds, such as immune stimulating agents, such as lentinan produced by fungal mycelium of the genus Lentinus, such as e.g. Lentinus edodes.

By fungal mycelium is intended any fungal biomass, which can be grown in submerged culture according to the invention. The fungal biomass may be in the form of single hyphae, spores, aggregates of mycelium, and partly differentiated mycelium.

Lentinan as used herein refers to the polysaccharide, which can be isolated from Lentinus edodes (Berk.) Sing. The primary structure is a $\beta$-1,3-D-glucan having $2\beta$-1,6-glucopyranoside branchings for every 5 $\beta$-1,3 linear linkages. The molecular weight may vary from 400,000 to 800,000 (Merck Index $12^{th}$ Edition, 1996, Monograph No 5462).

The cultivation of the fungal mycelium, such as fungi of the genus Lentinus, such as Lentinus results in the production of one or more extracellular agents, such as e.g. immune stimulating agents, in the form of e.g. a polysaccharide, such as e.g. a beta-glucan, including lentinan isolatable from Lentinus edodes, a polypeptide, a glycosylated polypeptide or a proteinacious polysaccharide compound, a proteoglucan, such as e.g. a polypeptide associated alpha-glucan or a polypeptide associated alpha-mannan, including KS-2 isolatable from Lentinus edodes, a lipid, or a secondary metabolite, which can be isolated and/or purified, and optionally fractionated, from the extracellular fraction of the fermentation broth of a bioreactor following cultivation of the basidiomycete fungal mycelium in question.

The extracellular fraction of the liquid fermentation medium is also termed the supernatant and this fraction can be separated from the fungal mycelium by e.g. centrifugation or filtration, or indeed by any other means available for obtaining a liquid fraction essentially without any fungal mycelium present therein. The term "essentially without any fungal mycelium present therein" shall denote that the concentration of fungal mycelium, including fractions thereof, has been reduced at least by a factor of $10^3$, such as reduced by a factor of at least $10^4$, for example a factor of at least $10^5$, such as reduced by a factor of at least $10^6$.

Besides being easier to isolate and process, fungal extracellular agents such as immune stimulating agents according to the present invention are surprisingly more potent than fungal associated agents, i.e. agents being either fungal intracellular agents, or agents which are removed from a liquid fermentation broth along with the removal of the fungal mycelium and fractions thereof by filtration, precipitation, or otherwise.

In a further aspect the invention relates to an immune stimulating agent obtainable from the extracellular part of the liquid growth medium according to the method of producing said immune stimulating agent.

This immune stimulating agent has surprisingly turned out to have a higher immunostimulating activity than the corresponding extract obtainable from the mycelium of the fungus, although the mycelium is known as the primary source of e.g. lentinan. In a particularly preferred embodiment, this extract is obtainable by removal of mycelium, removal of water from the medium, one or more rounds of precipitation with alcohol and washing with acid and/or base.

According to the invention there is also provided a composition comprising the immune stimulating agent obtainable as described above and a physiologically acceptable carrier. Furthermore, there is provided a pharmaceutical composition comprising the immune stimulating agent according to the invention and a pharmaceutically acceptable carrier. The pharmaceutical composition may in particular be used for treatment or prophylaxis in connection with an immune compromised condition.

Fungi belonging to the genus of *Lentinus*, such as *Lentinus edodes* represent one example of fungi according to the present invention. In other preferred aspects of the invention a method is provided wherein the fungus is selected from the group of fungi consisting of *Auricularia auricula-judae, Coriolus versicolor, Grifola frondosa, Flammulina velutipes, Schizophyllum commune, Sclerotinia scleroticum, Trametes versicolor, Tremella fuciformis, Agaricus blazei, Cordyceps sinensis, Ganoderma lucidum, Hericium erinaceus, Ionotus obliquus, Pleurotus ostreatus*, and *Polyperus umbellatus*.

DETAILED DESCRIPTION OF THE INVENTION

For the method of the present invention, "liquid-state" cultivation of *Lentinus* mycelium, or fractions thereof, is used. In short, this involves dissolving in water the nutrient compounds a microbial organism such as fungal mycelium, or fractions thereof, require for growth, transferring the solution to a bioreactor and inoculating the bioreactor with cells or spores of the microbial organism such as a fungal mycelium, or fractions thereof, to be cultivated. This is done under sterile conditions and with control of the environment in order to give the microbial organism a suitable chemical and physical environment. The technology related to "liquid-state" cultivation of microbial organisms is well known for the skilled person.

The advantage of "liquid-state" as compared to "semi-solid-state" or "solid-state" cultivation is that "liquid-state" proceeds more rapidly, is more effective with respect to conversion of the raw materials to products, and most importantly, it offers greater possibilities for controlling the growth conditions and thereby the reproducibility and the predictability of the process.

What distinguishes the various "liquid-state" processes from one another is the microbial organisms which are used and the cultivation conditions. For production of lentinan the microbial organism will be *Lentinus edodes* which is cultivated under the conditions described below. During "liquid-state" culture the medium with the fungal biomass is preferably agitated to reduce the occurrence of gradients and to ensure oxygen availability to the submerged cells. When microbial organisms are grown in a bioreactor, oxygen may be supplied to the liquid medium and the level of dissolved oxygen may be controlled by known methods.

Provided in one preferred embodiment is a method for production of lentinan, characterised by cultivating mycelium from *Lentinus edodes* in a liquid growth medium comprising one or more typical ingredients required for growth of microbial organisms such as malt extract, yeast extract, peptone, glucose, sucrose, salts providing phosphate, magnesium and potassium, corn-steep liquor and vitamins such as thiamine. More preferably, the medium comprises malt extract, yeast extract, peptone and glucose for mycelium growth and production of lentinan.

For inoculation of the growth medium, *Lentinus edodes* mycelium from agar plates containing malt extract, yeast extract, peptone and glucose can be used. *Lentinus edodes* can initially be cultivated on agar plates comprising the above nutrient compounds supporting the growth of the fungus. The plates are inoculated with mycelium from *Lentinus edodes* and incubated at least until a visible growth is evident on the plates, this can take from about 7 days to about 24 days or from about 10 to 30 days, typically 14 days or up to 20 days, at a temperature in the range of from 18 to 32° C., preferably in the area of from 22 to 31° C., such as a temperature of about 23° C., for example 24° C., such as 25° C., for example 26° C., such as 27° C., for example 28° C., such as 29° C., for example 30° C. The temperature may also be from 18 to 37° C., preferably from 23 to 32° C. such as about 28° C.

As an alternative to inoculation with mycelium from agar plates, inoculation of the growth medium can be carried out by using *Lentinus edodes* mycelium from a fermentation broth in e.g. a shake flask medium comprising nutrient compounds supporting cell growth. Shake flasks for cultivating *Lentinus edodes* can initially be inoculated with the mycelium which is cultivated on agar plates. The mycelium is scraped off the plates and transferred aseptically to shake flasks containing sterile water comprising dissolved nutrient compounds and nutrient salts supporting the growth of the fungal mycelium. A typical growth medium contains glucose, peptone, yeast extract and malt extract. The amount of inoculation material which gives the highest production of extracellular lentinan can be selected following initial experiments.

The shake flasks can be incubated by shaking for 6 to 21 days, preferably from 7 to 18 days, more preferably from 8 to 14 days at a temperature in the range of from 18 to 32° C., preferably in the area of from 22 to 31° C., such as a temperature of about 23° C., for example 24° C., such as 25° C., for example 26° C., such as 27° C., for example 28° C., such as 29° C., for example 30° C. The shake flasks may also be incubated from 8-25 days, more preferably from 10-20 days, more preferably from 12-18 days. The temperature may also be from 18 to 37° C., preferably from 23 to 32° C. such as about 28° C.

The content of the shake flasks can be used for inoculating a bioreactor. In that case, the reactor comprises a sterile solution of nutrient compounds and nutrient salts in water for mono-culture cultivation of basidiomycete fungal mycelium, or fractions thereof, such as *Lentinus* fungal mycelium, such as *Lentinus edodes*.

The bioreactor fermentation period is typically in the range of from 50 hours to 300 hours, preferably in the range of from 80 hours to 270 hours, and the temperature is kept constant in the range of 18 to 32° C., preferably in the area of from 22 to 31° C., such as a temperature of about 23° C., for example 24° C., such as 25° C., for example 26° C., such as 27° C., for example 28° C., such as 29° C., for example 30° C. The temperature may also be from 18 to 37° C., preferably from 23 to 32° C. such as about 28° C.

The reactor is fitted with an inlet for supplying air to the fermentation broth, and the fermentation broth is preferably kept under continuous agitation either as a result of the addition of air, or by means of a mixer device suitable for providing a good mixing of the content of the reactor.

It is preferred to adjust the pH of the growth medium to from about 3 to about 7, such as a pH of from about 4.5 to about 6.5, for example a pH of about 6, before the growth medium is inoculated with fungal mycelium, or fractions thereof, such as *L. edodes* mycelium. After the initial adjustment, pH may be dropped naturally during the course of the fermentation, or controlled at a particular value in the range pH 3 to 7, using addition of suitable pH-control agents, such as acid and base. The temperature of the growth medium is preferably in the range of from 18 to 32° C., preferably in the area of from 22 to 31° C., such as a temperature of about 23° C., for example 24° C., such as 25° C., for example 26° C., such as 27° C., for example 28° C., such as 29° C., for example 30° C. The temperature may also be from 18 to 37° C., preferably from 23 to 32° C. such as about 28° C.

Samples can be obtained from the bioreactor and analysed for biomass, metabolic products and nutrient compounds, the determinations of which can assist the operator of the bioreactor in the running of the fermentation process. Typical analyses routinely carried out are determination of biomass, residual sugar concentration and extracellular agent concentration, such as lentinan concentration in the case of *Lentinus* including *Lentinus edodes*. A person skilled in the art knows the methods for analysis which can be employed in this respect.

In the case of cultivation of *Lentinus edodes*, extracellular lentinan may be removed from the liquid growth medium by precipitation with e.g. alcohol, or by other means which result in the isolation and/or purification of microbial polysaccharides. It is an important aspect of the present invention that such isolation from the growth medium is performed with gentle methods and is generally carried out at temperatures around room temperature. Therefore the extracted compounds are not degraded or converted as may often be the case when using harsh extraction conditions for extracting compounds from the mycelium or from the fruiting bodies of *Lentinus edodes*.

*Lentinus edodes* deposited under IHEM 18992 with the Belgian Coordinated Collections of Microorganism (BCCM), 14 Rue J. Wytsman, B-1050 Bruxelles, Belgium, represents one preferred strain of *Lentinus edodes*. Further strains of *Lentinus edodes* are available from culture collections such as ATCC (American Type Culture Collection, P.O. Box 1549, Manassas, Va. 20108, USA), CBC (Centraalbureau voor Schimmelcultures, PO Box 85167, 3508 AD Utrecht, THE NETHERLANDS) and DSMZ (Deutsche Sammlung von Mikroorganismen and Zellkulturen GmbH, Mascheroder Weg 1b, 38124 Braunschweig GERMANY).

Additionally relevant *Lentinus* species, besides *Lentinus edodes*, includes *Lentinus* species such as: *Lentinus albovelutinus* G. Stev. (1964)=*Rhodocybe albovelutina* (G. Stev.) E. Horak (1971); *Lentinus anthocephalus* (Lév.) Pegler; *Lentinus badius* Bres.; *Lentinus castoreus* Fr. (1838)=*Lentinellus ursinus* (Fr.) Kühner (1926); *Lentinus chrysopeplus* Berk. & M. A. Curtis (1869)=*Cyptotrama asprata* (Berk.) Redhead & Ginns (1980); *Lentinus cochleatus* Fr.; *Lentinus concinnus* Pat.; *Lentinus delicatus* G. Stev. (1964)=*Marasmius delicatus* (G. Stev.) E. Horak (1971); *Lentinus fasciatus* Berk.; *Lentinus hepatotrichus* Berk. (1859)=*Lentinellus ursinus* (Fr.) Kühner (1926); *Lentinus hyracinus* Kalchbr. (1880)=*Lentinellus ursinus* (Fr.) Kühner (1926); *Lentinus lepideus* sensu Colenso (1891); *Lentinus lepideus* (Fr.) Fr. (1825)=*Lentinus suffrutescens* (Brot.) Fr. (1825); *Lentinus novaezelandiae* Berk. (1855)=*Lentinellus ursinus* (Fr.) Kühner (1926); *Lentinus pulvinulus* Berk. (1859)=*Lentinellus pulvinulus* (Berk.) Pegler (1965); *Lentinus punctaticeps* Berk. & Broome (1883); *Lentinus punctaticeps* cf. sensu Petersen, Nicholl & Hughes (1997); *Lentinus pygmaeus* Colenso (1887)=*Lentinus zelandicus* Sacc. & Cub. (1887); *Lentinus sajor-caju* (Fr.) Fr.; *Lentinus squarrulosus* Mont.; *Lentinus strigosus* (Schwein.) Fr. (1825); *Lentinus suffrutescens* (Brot.) Fr. (1825); and *Lentinus tuber-regium* Fr.; *Lentinus zelandicus* Sacc. & Cub. (1887) (Ref: http://nzfungi.landcareresearch.co.nz).

Fungal Mycelium Extracellular Immunostimulants

Provided in one embodiment of the invention is an immune stimulating agent, preferably a polysaccharide or a glycosylated polypeptide, obtained from the cultivation of basidiomycete fungal mycelium such as *Lentinus* mycelium according to the method of the invention.

Provided in another embodiment of the invention is the use of an extracellular agent such as lentinan in a method for stimulating the immune system of an individual in need of such stimulation. The lentinan is administered e.g. orally or subcutaneously to the individual in a pharmaceutically effective amount capable of stimulating the immune system of the individual. The stimulation of the immune system can be demonstrated by e.g. increased antibody production, by activation of helper T-cells, or by increased production of interleukins such as Interleukin 1 and Interleukin 2.

Provided in yet another embodiment of the invention is the use of an extracellular agent such as lentinan in the manufacture of a medicament for treating an immune compromised condition in an individual in need of such treatment. An immune compromised condition in an individual is demonstrated e.g. by an insufficient amount of antibodies, or a decreased antibody production, by an insufficient amount of helper T-cells, or a decreased production of helper T-cells in the individual, or by an insufficient amount of interleukins such as Interleukin 1 and Interleukin 2, or a decreased production of interleukins such as Interleukin 1 and Interleukin 2 in the individual.

"Insufficient amount" and "decreased production" as used herein above shall denote such amounts and productions which a medical expert considers as being below a predetermined level or value normally associated with a healthy individual. The amount and/or production will generally depend on factors such as age, general physical condition, and the like. For this reason a predetermined level or value shall be determined on an individual basis by a medical expert. One indication of an immune compromised condition in an individual is a gradually decreasing number of antibodies, a gradually decreasing number of CD4 (positive) cells, or a gradually decreasing number of T-helper cells per unit (blood) sample volume measured over time, such as days, weeks, months or years.

Additional examples of extracellular immunostimulants includes, but is not limited to, β-(1,3), β-(1,6) D-glucans, schizophyllan, grifolan, coriolan and Coriolus versicolor glycosylated polypeptides such as PSK and PSP, polypeptides associated with alpha-mannan such as KS-2 isolatable from *Lentinus edodes*, and reishi isolatable from *Ganoderma lucidum*. Reference is made to Table 1 herein below for a further detailed description of the structure and composition of the above extracellular immunostimulants.

Preferred immunostimulating agents produced by fungal mycelium of the invention are polysaccharides such as polysaccharides comprising a β-D-glucan backbone (i.e. linear polymers of D-glucose with other monosaccharides), or β-D-glucans linked to proteins (so-called polysaccharide-peptides, or "proteoglucans"). The preferred polysaccharides are homopolymers. The basic β-D-glucan is a repeating structure with its D-glucose molecule joined by linear chains by β-bonds from the carbon 1 of one saccharide ring to the carbon 3 of the next (β-1,3), from carbon 1 to carbon 4 (β-1,4), or from carbon 1 to carbon 6 (β-1,6). The best know immune stimulating compound produced by *Lentinus edodes* is lentinan. This is β-(1,3) D-glucan with β-(1,6) side chains. The chain length varies with the typical product having a molecular weight in the range 400,000-1,000,000 g/mol. Further preferred polysaccharides are listed in Table 1.

For a determination of the immunostimulating characteristics of an extracellular agent such as e.g. lentinan, the following method can be used: 12 weeks old Sprague Dawley rats receive 1 mg of test compound which have been extracted from the fermentation broth in 0.5 ml 0.09 saline (i.p.) 2 days before the immunisation. Control animals receive 1 mg casein. The animals are immunised with BSA (0.5 mg) in 0.25 "Freunds Complete Adjuvant" and blood samples are obtained after 11 days for measurement of the antibody response. The specific anti-BSA antibody concentration is determined against an absolute standard of antibody BSA by means of "sandwich" ELISA. A typical result of the immunostimulating activity of intracellular and extracellular lentinan is shown in Table 7a and 7b.

Additional Fungal Mycelium Extracellular Agents and Uses Thereof

Further additional preferred embodiments of the present invention relate to extracellular agents, other than immunostimulating agents, produced by a number of fungi, as well as to methods for producing said agents and methods for using said agents.

The fungi of particular interest to the present invention include *Lentinus edodes, Ganoderma lucidum, Auricularia auricula-judae, Coriolus versicolor, Grifola frondosa, Flammulina velutipes, Schizophyllum commune, Sclerotinia scleroticum, Trametes versicolor, Tremella fuciformis, Agaricus blazei, Cordyceps sinensis, Ganoderma lucidum, Hericium erinaceus, Ionotus obliquus, Pleurotus ostreatus*, and *Polyperus umbellatus*.

The above fungal mycelium can be cultivated in monoculture in a bio-reactor under suitable growth conditions allowing growth and propagation of the fungal mycelium in question. The growth conditions cited herein for *Lentinus edodes* can also be used for the above fungal mycelium.

Besides extracellular fungal immune stimulating agents, such as extracellular proteinacious compounds, including glycosylated polypolypeptides, such as the alpha-mannan polypeptide KS-2, and extracellular polysaccharides, such as extracellular lentinan produced by *Lentinus edodes*, the fungal microbial organisms of the invention, such as e.g. *Ganoderma lucidum, Auricularia auricula-judae, Coriolus versicolor, Grifola frondosa, Flammulina velutipes, Schizophyllum commune, Sclerotinia scleroticum, Trametes versicolor, Tremella fuciformis, Agaricus blazei, Cordyceps sinensis, Ganoderma lucidum, Hericium erinaceus, Ionotus obliquus, Pleurotus ostreatus*, and *Polyperus umbellatus* are also capable of extracellularly producing agents having additional desirable effects.

TABLE 1

Extracellular agents, including structure and composition, produced by the selected fungi.

| Fungus | Extracellular agent | Structure and composition |
|---|---|---|
| *Schizophyllum commune* | schizophyllan | β-(1,3), β-(1,6) D glucan |
| *Grifola frondosa* | grifolan | β-(1,3), β-(1,6) D glucan |
| *Coriolus versicolor* | PSK, PSP | Polypeptides attached to polysaccaride β-D glucan chains. The polysaccharide chains are true glucans, mainly 1,4; 1,2 and 1,3 glucose linkages |
| *Lentinus edodes* | KS-2 | Polypeptide associated α-mannan |
| *Lentinus edodes* | lentinan | β-(1,3), β-(1,6) D glucan |
| *Ganoderma lucidum* | reishi | The basic structure of the major bioactive Ganoderma glucans β-(1,3), β-(1,6) D glucan is β-(1,3) D-glucopyronan with 1-5 units of β-(1,6) monoglucosyl side chains |

The effects associated with the above extracellular agents produced by the fungi of the invention are e.g. analgesic effects, anti-allergic activity, bronchitis-preventative effects, anti-inflammatory activity, anti-bacterial properties (against Staphylococci, Streptococci and Bacillum pneumoniae), antioxidant effects, antitumor activity, blood pressure lowering effects, bone marrow formation enhancing effects, cardiotonic activity (i.e. lowering serum cholesterol and/or increasing myocardial metabolism and/or improving coronary artery hemodynamics), natural killer cell enhancing effects, expectorant and antitussive properties, immunopotentiation activities, anti-HIV activities, adrenocortical improving effects, Interleukin-1, Interleukin-2, and Interleukin-3 stimulating effects, liver-protective effects and detoxifying effects, ionizing radiation protecting effects, anti-ulcer activity, and agents having the effect of increasing white blood cells and hematoglobin in peripheral blood.

The above effects can be demonstrated clinically in animals including human beings having been treated with a pharmaceutically effective amount of an extracellular agent isolated from a fungal mycelium according to the invention.

Method of Treatment

In one aspect the invention relates to a method of treatment of an individual diagnosed with an immune compromised condition, said method comprising the steps of administering to said individual the composition according to the invention or the pharmaceutical composition according to the invention in an amount effective in treating said immune compromised condition.

The administered amount may in be an amount effective in prophylactically treating said immune compromised condition.

Also provided is a method of treatment of an individual recovering from surgery or illness and at risk of contracting an immune compromised condition, said method comprising the steps of administering to said individual the composition according to the invention or the pharmaceutical composition according to the invention in an amount effective in boosting the immune system of said individual.

Furthermore a method of treatment of an individual diagnosed with or at risk of contracting acquired immunodeficiency syndrome is provided, said method comprising the steps of administering to said individual the composition according to the invention or the pharmaceutical composition according to the invention in an amount effective in treating or prophylactically treating said syndrome.

The immune compromised condition may be selected from the group consisting of an infectious disease, a parasitic disease, haemophilus meningitis, pneumococcal meningitis, streptococcal meningitis, staphylococcal meningitis, meningitis due to other organisms, encephalitis, viral pneumonia, pneumococcal pneumonia, other bacterial pneumonia, pneumonia due to other specified organisms except bacteria, bronchopneumonia, organism unspecific pneumonia, influenza, unspecified diarrhea, hepatitis unspecified, acute and subacute necrosis of the liver, chronic hepatitis, and abscess of liver.

Furthermore, the immune compromised condition may be an infectious or parasitic disease caused by, or selected from, cholera, salmonella, shigellosis, *Escherichia coli*, intestinal infection due to other specified bacteria, *Clostridium difficile*, viral gastroenteritis, infectious colitis, enteritis and gastroenteritis, infectious diarrhea, tuberculosis, listeriosis, pasteurellosis, mycobacterium, diphtheria, pertussis, meningococcus, *streptococcus* septicaemia, *staphylococcus* septicaemia, pneumococcal septicaemia, septicaemia due to anaerobes, septicaemia due to other gram-negative organisms, actinomycotic infection, gas gangrene, toxic shock syndrome, necrotizing faciitis, Friedlander's bacillus, haemophilus influenzae, *pseudomonas*, AIDS/HIV infections, acute poliomyelitis, Creutzfeldt-Jacob disease, subacute sclerosing panencephalitis, progressive multifocal leucoencephalopathy, unspecified slow virus infection of the central nervous system, coxsackie virus, unspecified viral meningitis, lymphocytic choriomeningitis, unspecified viral encephalitis, chickenpox, herpes zoster, herpes simplex, viral hepatitis 'A', viral hepatitis 'B', other specified viral hepatitis, chronic hepatitis, abscess/acute necrosis of liver, infectious mononucleosis, cytomegalic inclusion disease, chlamydiae, adenovirus, viral infection, syphilis, *candida*, unspecified histoplasmosis, aspergillosis, cryptococcosis, mycoses, strongyloidiasis, intestinal parasitism, toxoplasmosis, sarcoidosis, pneumocystis carinii, post polio syndrome, haemophilus meningitis, pneumococcal meningitis, streptococcal meningitis, staphylococcal meningitis, encephalitis, pneumonia due to adenovirus, pneumonia due to respiratory syncytial virus, pneumonia due to parainfluenza virus, pneumonia due to other virus, viral pneumonia, pneumococcal pneumonia, pneumonia due to klebsiella pneumoniae, pneumonia due to pseudomonas, pneumonia due to haemophilus influenzae, pneumonia due to streptococcus, pneumonia due to staphylococcus, and bacterial pneumonia.

The individual may be a mammal including a human being.

The pharmaceutical composition according to the invention may also be used in the manufacture of a medicament for treatment of an immune compromised condition of an individual in need of such treatment. The immune compromised condition may be any of those disclosed above. The treatment may be prophylactic, ameliorating or curative.

The composition and the pharmaceutical compositions according to the invention may also form part of a kit comprising said compositions and a dosage regime instruction with guidelines for dose and time administration.

Purification and Isolation of Extracellular Agents

The extracellular agents such as e.g. lentinan can be isolated from the extracellular growth medium following a fermentation of e.g. *Lentinus* fungal mycelium, or part thereof, in a liquid growth medium.

Isolation can occur by alcohol precipitation using 70% alcohol or 96% alcohol. Suitable alcohols are C1 to C5 aliphatic alcohols, such as methanol, ethanol, propanol, iso-propanol, n-butanol, iso-butanol, n-pentanol. The ratio between the volume of extracellular growth medium and alcohol can vary from 5:1 to 1:5, such as 4:1, 3.1, 2:1, 1:1, 1:2, 1:3, 1:4, and 1:5 depending on the concentration of alcohol and the length of the carbon chain.

It is also possible to obtain from the precipitated fraction of extracellular agents a fraction of such agents, including polysaccharides, by subjecting the alcohol precipitated extracellular agents such as polysaccharides to one or more steps selected from desalting, washing with an acidic solution, washing with a basic solution, ion exchange chromatography, and gel filtration, including any combination thereof. Desalting can be carried out using a suitable column or by dialysis; suitable acidic solutions are diluted strong acids having a pH of from about 1 to about 7, such as a pH of from about 2 to about 6; suitable basic solutions are diluted strong bases having a pH of from about 7 to about 11, such as a pH of from about 8 to about 10. Weak acids and weak bases can also be used for the washing step, as can 70% ethanol when e.g. 96% ethanol has been used for the precipitation.

Ion exchange chromatography and/or gel filtration are preferably used after desalting and/or washing of the precipitate. By using such steps, one can obtain fractions comprising extracellular agents having a molecular weight of from about 10,000 g/mol to about 20,000 g/mol, extracellular agents having a molecular weight of from about 20,000 g/mol to about 40,000 g/mol, extracellular agents having a molecular weight of from about 40,000 g/mol to about 60,000 g/mol, extracellular agents having a molecular weight of from about 60,000 g/mol to about 80,000 g/mol, extracellular agents having a molecular weight of from about 80,000 g/mol to about 100,000 g/mol, extracellular agents having a molecular weight of from about 100,000 g/mol to about 150,000 g/mol, extracellular agents having a molecular weight of from about 150,000 g/mol to about 200,000 g/mol, extracellular agents having a molecular weight of from about 200,000 g/mol to about 300,000 g/mol, extracellular agents having a molecular weight of from about 300,000 g/mol to about 400,000 g/mol, extracellular agents having a molecular weight of from about 400,000 g/mol to about 500,000 g/mol, extracellular agents having a molecular weight of from about 500,000 g/mol to about 600,000 g/mol, extracellular agents having a molecular weight of from about 600,000 g/mol to about 700,000 g/mol, extracellular agents having a molecular weight of from about 700,000 g/mol to about 800,000 g/mol, extracellular agents having a molecular weight of from about 800,000 g/mol to about 900,000 g/mol, and extracellular agents having a molecular weight of from about 900,000 g/mol to about 1,000,000 g/mol.

The purification can also involve steps actively seeking to remove e.g. proteinacious substances from e.g. a polysaccharide fraction. This can be achieved by proteolytic degradation by e.g. proteinase K. Lipids can be removed from a fraction by treatment with lipase or esterase. Undesirable polysaccharides can be removed by treatment with enzymes such as glucanases, amylases, and the like.

The purity of an isolated fraction of extracellular agents can be determined by e.g. chromatography or spectroscopy.

One way to isolate an extracellular agent is to modify the method described by Chihara et at (1970): Fractionation and purification of the polysaccharide with marked antitumor activity, especially lentinan from *Lentinus edodes* (Berk) Sing. (An edible mushroom). Cancer research, 30, 2776-2781. According to the present invention, fungal biomass is removed from the broth with filtration and the volume of the filtrate reduced to 10-20% of the original volume by evaporation. A solvent is then added to the concentrated liquid until precipitation of the product is achieved. Solvents include alcohols such as methanol, ethanol, butanols and propanols, as well as various ketones. The precipitate is re-suspended and washed with alkali and acids as well as the solvent before final drying.

EXAMPLES

The following examples illustrate preferred embodiments of the invention and should not be construed so as to limit the invention to the embodiments and technical results disclosed in the examples.

Example 1

Shake Flask Experiments

A medium composed of glucose, malt extract, yeast extract and peptone in various concentrations was used for cultivating *Lentinus edodes* for achieving fungus growth and lentinan production in 500 ml shake flasks containing 200 ml of medium. The content of the various media is shown in Table 2. The flasks were shaken for 16 days at 28 degrees Centigrade.

TABLE 2

Composition of media for shake flask experiments

| Medium | Malt extract (%) | Yeast extract (%) | Peptone (%) | Glucose (%) |
|---|---|---|---|---|
| 1 | 0.3 | 0.3 | 0.5 | 1.0 |
| 2 | 0.3 | 0 | 0.5 | 1.0 |
| 3 | 0 | 0.3 | 0.5 | 1.0 |
| 4 | 1.0 | 0.3 | 0.5 | 0 |
| 5 | 0.3 | 0.3 | 0.5 | 2.0 |
| 6 | 0.3 | 0.3 | 0.5 | 4.0 |
| 7 | 0 | 0 | 0.5 | 1.0 |

All media are adjusted to pH 6

The resulting production of fungus mass and lentinan is shown in Table 3:

| Medium | Biomass (g/l) | Lentinan (mg/l) |
|---|---|---|
| 1 | 2.4 | 42 |
| 2 | 0.9 | 15 |
| 3 | 1.1 | 14 |
| 4 | 0.2 | 0 |
| 5 | 2.3 | 43 |
| 6 | 1.8 | 33 |
| 7 | 0.3 | 0 |

The maximum amount of biomass and lentinan was produced when all medium components were present. Omission of one of the components resulted in reduced growth and lentinan production. The same thing happened if the concentration of glucose became too high.

Example 2

Bioreactor Experiments

For these experiments, a 10-liter bioreactor with stirring equipment was used. The reactor was sterilized and filled with 6 liters of sterile medium. After pH adjustment to a value of about 6, the reactor was inoculated with the content of 16 days old shake flasks. Air was added to the reactors at a rate of 1 vvm (volume of air per volume of reactor per minute), the stirrer rotated at a rate of 200 rpm and the temperature was kept at approx. 28 degrees Centigrade.

A. Media Compositions

The various media used are shown in Table 4.

TABLE 4

Composition of media used in bioreactor experiments

| Medium | Malt extract (%) | Yeast extract (%) | Peptone (%) | Glucose % |
|---|---|---|---|---|
| A | 0.3 | 0.3 | 0.5 | 1.0 |
| B | 0.3 | 0.3 | 0.5 | 2.0 |
| C | 0.3 | 0.3 | 1.0 | 1.0 |

The resulting concentration of biomass and lentinan achieved is shown in Table 5.

TABLE 5

Biomass and lentinan in a bioreactor with different media

| Medium | Fermentation time[1] (hours) | Biomass (g/l) | Lentinan (g/l)[2] |
|---|---|---|---|
| A | 88 | 3.97 | 0.17 |
| B | 240 | 3.62 | 0.23 |
| C | 211 | 3.48 | 0.10 |

[1]For maximum lentinan concentration
[2]Containing extracellular as well as extracted intracellular lentinan.

Apparently, there is little variation in the produced amount of biomass and lentinan achieved by means of the different media. It was observed, however, that the lag time of the fermentation process was considerable. This is unproductive time and it is usual practice to reduce the lag time by varying the amount of inoculation material used.

B. Variation of Amount of Inoculation Material Used in Bioreactor Experiments.

The result of using different amounts of inoculation material is shown in Table 6:

TABLE 6

Production of biomass and lentinan in a bioreactor with different amounts of inoculation material

| Amount of inoculum (%) | Fermentation time[1] (hours) | Biomass (g/l) | Lentinan (g/l)[2] |
|---|---|---|---|
| 15 | 144 | 3.07 | 0.07 |
| 30 | 88 | 3.97 | 0.17 |

[1]For maximum lentinan concentration
[2]Contains extracellular as well as extracted intracellular lentinan The present results show that by changing the amount of inoculation material used and the composition of the fermentation medium, it is possible to affect the growth of *Lentinus*

*edodes* and lentinan production. We have demonstrated that it is possible to upgrade the cultivation of *L. edodes* from shake flasks to a bioreactor. The present experiments were carried out in a 10-liter reactor but there is no reason for restricting the process to the mentioned size.

The experiments show that by varying the amount of inoculation material, it is possible to affect both the lag time of the process and the amount of lentinan produced. Further experiments must be carried out for establishing the optimal amount of inoculation material.

The experiments with respect to the composition of nutrients in the growth medium show that for the growth of *L. edodes* and the production of lentinan, the medium may contain malt extract, yeast extract, peptone and glucose. The results show that there may be a relation between medium composition and production of lentinan. By increasing the concentration of glucose to 2%, the lag time is increased but not the rate of growth. This increase of the lag time also occurred in the production of lentinan, the production starting later at a high concentration of glucose, but the amount of extracellular lentinan produced was increased.

Example 3

Immunological Experiments

The result of immunological experiments with even amounts of intracellular and extracellular material from the fermentation broth, used as described above, is presented in Table 7.

After fermentation the biomass was separated from the rest of the fermentation broth by filtration. It was then added to 1 liter of distilled water and this mixture was heated in an autoclave at 121° C. for two hours. The mixture was subsequently filtered and the volume of the filtrate was reduced by boiling to around 10% of the original volume. When this had cooled to room temperature, around 2 volumes of absolute ethanol was added to precipitate the product. The precipitate was removed and washed with absolute ethanol, re-suspended in distilled water and homogenised. Thereafter, 200 ml of 0.2 M cetyltrimethyl ammonium bromide and 0.2 M sodium hydroxide was added and the mixture was stirred well and kept at 4° C. for 18 hours. The precipitate was thereafter removed and washed with absolute ethanol. Then, 50 ml of a 20% glacial acetic acid was added to the filtrate and the mixture was stirred. The precipitate was subsequently removed, washed well and dried under vacuum.

The first filtrate after the fermentation (fermentation broth less the biomass) went though the same steps from reducing the volume by boiling onwards. Thus the only step the extracellular product did not go through was being kept at 121° C. for two hours.

For a determination of the immunostimulating characteristics, the following method was used: 12 weeks old Sprague Dawley rats received 1 mg of test compound which had been extracted from the fermentation broth in 0.5 ml 0.09 saline (i.p.) 2 days before the immunisation. Control animals received 1 mg casein. The animals were immunised with BSA (0.5 mg) in 0.25 "Freunds Complete Adjuvant" and blood samples were obtained after 11 days for measurement of the antibody response. The specific anti-BSA antibody concentration was determined against an absolute standard of antibody BSA by means of "sandwich" ELISA.

TABLE 7a

Immune response (measured in anti-BSA Ig production) in rats treated with lentinan

| Sample | Anti-BSA Ig (µg/ml serum) |
| --- | --- |
| Control | 9 |
| Intracellular lentinan | 19 |
| Extracellular lentinan | 24 |

TABLE 7b

Immune response (measured in anti-BSA Ig production) in rats treated with lentinan (corrected numbers)

| Treatment | anti-BSA Ig (µg/ml serum) |
| --- | --- |
| Control | 9 |
| Cellular lentinan | 16 |
| Extracellular lentinan | 26 |

The data in Table 6b have been corrected.

The results of the immunological experiments shows that lentinan is a very active stimulator of the immune system. The extracellular product provides a higher response than intracellular lentinan. It is, therefore, desirable to optimise the fermentation process for the production of extracellular lentinan. Extraction of intracellular lentinan is costly with respect to time, personnel and chemicals. It is, however, very simple to remove the extracellular product from the fermentation broth as methods for the precipitation of a polysaccharide can be used, for example by means of various types of alcohol.

Example 4

Shake Flask Experiments

A medium composed of 15 g/l glucose, 3 g/l malt extract, 3 g/l yeast extract and 5 g/l peptone was used for cultivating *Lentinus edodes* to obtain fungus growth and lentinane production in 500-ml shake flasks containing 200 ml of medium. The flasks were shaken at 28 degrees Centigrade for a given number of days and the concentration of biomass and lentinan, respectively was measured. Typical results are given in Table 7 given below.

TABLE 7

Shake Flask Experiments

| Biomass (g/l) | Extracellular Product (g/l) | Fermentation time (days) |
| --- | --- | --- |
| 1.33 | 65 | 14 |
| 5.0 | 53 | 22 |

Extending the fermentation time led to more biomass but the concentration of extracellular product did not show a concomitant increase. It may be that degradation of the product became more dominant during the extended fermentation time allowed.

Example 5

Bioreactor Experiments

The experiments were carried out in a 3-liter and a 10-liter bioreactor with stirring equipment. The reactor was sterilized and filled with 2 and 6 liters of sterile medium, respectively. Following pH adjustment to a value of about 6, the reactor was inoculated with the content of 7-8 days old shake flasks. Air was supplied to the reactors and the stirring equipment performed a good mixing of the reactor content. The temperature was kept at 28 degrees Centigrade. In the experiments reported here, the fermentation time was 7 days unless otherwise stated.

Under these conditions, the concentration of biomass (dry weight) can be up to 3 g/l and the concentration of isolated dried polysaccharide can be 200 mg/l. Typical results are given in Table 2.

TABLE 8

Typical Results from Bioreactor Experiment

| Biomass (g/l) | Extracellular Product (mg/l) | Comments |
|---|---|---|
| 2.5 | 100 | Glucose-based medium |
| 1.6 | 140 | Sucrose-based medium |

The invention claimed is:

1. A method for producing one or more water-soluble extracellular immune stimulating agents, said method comprising the steps of:
   i) cultivating a fungus of the genus *Lentinus edodes* in an aqueous liquid growth medium, wherein said cultivation results in accumulation of said one or more immune stimulating agents in the aqueous growth medium,
   ii) separating the fungal mycelium from said aqueous liquid growth medium by centrifugation or filtration to obtain an aqueous phase supernatant comprising said one or more immune stimulating agents, and
   iii) subjecting said aqueous phase supernatant, or a fraction thereof, comprising said one or more water-soluble immune stimulating agents to at least one size fractionation step resulting in the isolation of an aqueous phase isolate which comprises one or more immune stimulating agents comprising a polysaccharide having a molecular weight in the size range of from 100,000 g/mol to 1,000,000 g/mol;
   wherein said aqueous phase supernatant comprising said one or more immune stimulating agents is not subjected to alcohol precipitation, and
   wherein said isolation of the aqueous phase isolate does not degrade or convert said immune stimulating agents during the isolation.

2. The method of claim 1, wherein the immune stimulating agent consists of said Polysaccharide.

3. The method according to claim 1, wherein the liquid growth medium comprises one or more ingredients required for growth of microbial organisms selected from the group consisting of malt extract, yeast extract, peptone, glucose, sucrose, salts providing phosphate, magnesium and potassium, corn-steep liquor and vitamins.

4. The method according to claim 1, wherein the liquid growth medium is agitated and supplied with oxygen from an oxygen source.

5. The method according to claim 1, wherein the growth temperature is in the range of from 23° C. to 32° C.

6. The method of claim 1, wherein said one or more extracellular immune stimulating agents are immunologically distinct from an intracellularly produced immune stimulating agent.

7. The method of claim 1, wherein step (iii) is carried out at about room temperature.

8. The method of claim 1, wherein said isolate comprises one or more immune stimulating agents with a molecular weight in the range of from 150,000 g/mol to 1,000,000 g/mol.

9. The method of claim 8, wherein the isolate does not comprise any immune stimulating agent with a molecular weight outside the range of from 150,000 g/mol to 1,000,000 g/mol.

10. The method of claim 1, wherein said isolate comprises one or more immune stimulating agents with a molecular weight in the range of from 200,000 g/mol to 1,000,000 g/mol.

11. The method of claim 1, wherein said isolate comprises one or more immune stimulating agents with a molecular weight in the range of from 300,000 g/mol to 1,000,000 g/mol.

12. The method of claim 1, wherein said at least one size fractionation step is size exclusion chromatography or gel filtration.

* * * * *